(12) United States Patent
Roenneburg et al.

(10) Patent No.: US 7,259,370 B2
(45) Date of Patent: Aug. 21, 2007

(54) MIXING CHAMBER PROBE ADAPTOR

(75) Inventors: Lucas D. Roenneburg, Albany, WI (US); Kevin R. Fawcett, Ridgeway, WI (US)

(73) Assignee: Gilson, Inc., Middleton, WI (US)

( * ) Notice: Subject to any disclaimer, the term of this patent is extended or adjusted under 35 U.S.C. 154(b) by 22 days.

(21) Appl. No.: 11/150,838

(22) Filed: Jun. 10, 2005

(65) Prior Publication Data

US 2006/0016980 A1   Jan. 26, 2006

Related U.S. Application Data

(60) Provisional application No. 60/578,780, filed on Jun. 10, 2004.

(51) Int. Cl.
*H01J 49/00* (2006.01)
(52) U.S. Cl. .................... 250/288; 210/198.2
(58) Field of Classification Search .............. None
See application file for complete search history.

(56) References Cited

U.S. PATENT DOCUMENTS 5,578,157 A * 11/1996 Higdon .................. 156/278

OTHER PUBLICATIONS

Joan Stevens, PH.D., Luke Roenneburg, Tim Hegeman, Kevin Fawcett; Automated Sample Preparation /Concentration of Biological Samples Prior to Analysis via MALDI-TOF Mass Spectroscopy; Gilson, Inc. Application Note 222, Mar. 2004, pp. 1-9.
Joan Stevens, PH.D., Luke Roenneburg, Kevin Fawcett, Analysis of Peptides via Capillary HPLC and Fraction Collection Directly onto a MALDI Plate for Off-line Analysis by MALDI-TOF, Gilfson, Inc. Application Note 219, Nov. 2003, pp. 1-8.

* cited by examiner

*Primary Examiner*—David A. Vanore
(74) *Attorney, Agent, or Firm*—Foley & Lardner LLP

(57) ABSTRACT

A mixing chamber probe adaptor comprising a chamber connector and a probe connector is provided. The mixing chamber probe adaptor imparts a fixed spatial joining of a chamber to a probe and allows a mixing chamber to be received by the chamber connector. In some embodiments, the mixing chamber probe adaptor will be adapted to connect to a spring-loaded probe and receive a micro mixing tee. In other embodiments, the mixing chamber probe adaptor may be used with other types of chambers and probes.

17 Claims, 4 Drawing Sheets

MIXING CHAMBER PROBE ADAPTOR

CLAIM OF PRIORITY

This application claims priority from U.S. Provisional Patent Application No. 60/578,780, filed Jun. 10, 2004.

FIELD OF THE INVENTION

The present invention relates to a device for use when spotting a MALDI target. More particularly, the invention relates to a mixing chamber probe adaptor that joins a mixing chamber and MALDI target spotting probe in an automated MALDI spotting device.

BACKGROUND OF THE INVENTION

The recent employment of matrix-assisted-laser-desorption/ionization (MALDI) (Karas & Hillenkamp, Anal. Chem. 60, 2299 (1988)) with time-of-flight (TOF) mass spectrometry has extended the accuracy of mass spectrometric measurements to include proteins and nucleic acids. See generally, Kinter, Anal. Chem. 67, 493R-497R (1995); Schoneich et al, Anal. Chem. 67, 155R-181R (1995); Busch, J. Chromatog. A 692, 275-290 (1995); and Limbach et al, Curr. Opin. Biotechnol. 6, 96-102 (1995). Today, the sensitivity, mass range and ability to analyze complex mixtures has made mass spectrometry an important tool for the analysis of large biomolecules. Many researchers both in academic and industrial settings use MALDI as an integral part of biomolecule analyzing experimentation.

MALDI has many advantages over traditionally employed methods of large biomolecule analyzation, such as two-dimensional gel electrophoresis. For example, MALDI displays both high sensitivity and relatively high tolerance to the presence of sample contaminants. MALDI also has the ability to accurately measure biomolecules using only subpicomole amounts of analyte. Furthermore, MALDI may be automated, thus, making the technique less labor intensive and time consuming as compared to traditional analyzation methods. MALDI automation also allows handling of small analyte volumes, an advantage sought by many MALDI users. Furthermore, MALDI provides a means for repeat analyzation of a particular sample as it is destructive to only a minute portion of the sample. Thus, it leaves a massive amount of sample available for re-analysis. Other current techniques such as electrospray are sample destructive leaving no sample for repeat analysis.

Although MALDI has currently been automated to a certain degree, the completely successful automation of MALDI spotting, because of the extensive and exacting analyte sample preparation required, has proven difficult. Generally, in order to correctly prepare a MALDI analyte sample, MALDI matrix solution must be added to the analyte prior to analysis. Even following this addition, interpretable results necessitate the MALDI matrix solution and analyte be evenly distributed to produce a homogeneous analyte sample. Consequently, complete mixing of MALDI matrix solution and analyte is required to obtain a reliable analyte sample. As used herein, an analyte sample is a combination of analyte and an appropriately absorbing sample matrix solution.

In automated MALDI spotting, because the analyte sample is not vortexed, it is often difficult to achieve the degree of homogenization that results from the complete mixing of MALDI matrix solution and analyte during manual spotting. Complete homogenization is important as complete mixing provides a higher quality spot and eliminates "hot spots" in the target, making the MALDI target more uniform. The elimination of hot spots is essential to accurate MALDI experimentation, regardless of whether manual or automated MALDI is being performed. Although these hot spots may be eliminated by thorough vortexing in manual MALDI, a need exists to insure complete mixing of analyte sample when using automated MALDI spotting. In automated MALDI spotting, an important step toward ensuring complete mixing includes incorporating the use of mixing chambers. Using a mixing chamber during automated MALDI spotting increases the mixing of analyte and matrix solution, resulting in increased signal to noise ratios and fewer "hot spots."

Unfortunately, in the past, when these mixing chambers were used with particular types of sample dispensing probes, such as MALDI target spotting probes, certain problems arose. For example, when a mixing chamber is used with a spring loaded probe, because the tubing in the spring loaded probe moves during spotting of the MALDI plate, the tubing may easily kink and bend. This distortion of the tubing may result in MALDI targets that are not uniform, making the results harder to interpret. Furthermore, because of the extra weight placed on the tubing when a mixing chamber is used without a mixing chamber probe adaptor, the tubing may separate from the mixing chamber, either resulting in lost analyte, MALDI matrix, or in the case of tubing that separates the mixing chamber from the probe, lost analyte sample. But because spring loaded probes provide many advantages, such as eliminating direct contact between the probe and the MALDI plate and allowing accurate MALDI target deposition by handling small amounts of analyte sample with minimal loss, it is preferable to use spring loaded probes over other sample dispensing probes during automated MALDI spotting. The spring in the spring loaded probe allows tubing, not the spring loaded probe itself, to touch the MALDI plate when spotting a MALDI target. Although glass capillaries that directly touch the plate may be used to spot MALDI targets, their fragility and propensity to cause MALDI plate damage makes them less desirable than a spring loaded probe. Spring loaded probes cause less damage to both the probe itself and the MALDI plate. The use of spring loaded tubing to spot a MALDI target also results in more accurate MALDI targets, as a greater amount of a more uniform pattern of analyte sample is added to the MALDI plate. In addition, the spring loaded probe permits a lower dead volume in the system as a result of the tubing in the spring loaded probe directly touching the MALDI plate, thus eliminating analyte sample loss caused by probe surface tension. Consequently, a need exists for a solution to the problems created when using a mixing chamber with a spring loaded probe.

SUMMARY

This invention relates to a chamber probe adaptor for use in holding a chamber and a probe in a fixed spatial relationship. More specifically, this invention relates to a mixing chamber probe adaptor used to connect a mixing chamber to a spring loaded probe during automated MALDI plate spotting. In most embodiments, the mixing chamber probe adaptor is both flexible enough to allow easy reversible attachment or joining of the mixing chamber to the probe and strong enough to maintain the chamber and the probe in a fixed spatial relationship.

Although the mixing chamber probe adaptor of the present invention is not limited to use in joining mixing chambers with spring loaded probes, in one aspect of the invention, the mixing chamber probe adaptor allows reversible connection of a mixing chamber and a spring loaded probe, wherein both the mixing chamber and the spring loaded probe are adapted to be used with an automated apparatus for spotting a MALDI target. Generally, an automated apparatus for spotting a MALDI target comprises an XYZ robot, a deposition device, which may be a probe or nebulizer, a flow control device (either a syringe pump or piston pump) and an optional mixing chamber.

Not all MALDI spotters have the ability to apply mixed matrix and analyte together. According to the invention, the mixing chamber probe adaptor may be used to join any applicable mixing chamber and probe, nevertheless, the embodiments where the mixing chamber probe adaptor is used with a mixing chamber and a spring loaded probe are especially valuable. This value flows from the advantages provided by spring loaded probes in automatic MALDI plate spotting. Although one of skill in the art understands that embodiments of the invention may be used with any type of sample dispensing probe, for example probes used in various microarrays, the embodiments of the invention shown in the figures demonstrate use of the invention with spring loaded probes.

Generally the mixing chamber probe adaptor that can be used with the spring loaded probe comprises a chamber connector adapted to connect to the chamber, which may be a mixing chamber, and a probe connector adapted to connect to a sample dispensing probe, which may be a spring loaded probe. In specific embodiments, the chamber connector may comprise a C-shaped sleeve with a tubular cavity for accepting the chamber and the probe connector may be adapted to connect to a spring-loaded probe.

The above described advantages and embodiments are set forth in the following description and illustrated in the drawings described below.

DETAILED DESCRIPTION

Figure 1:
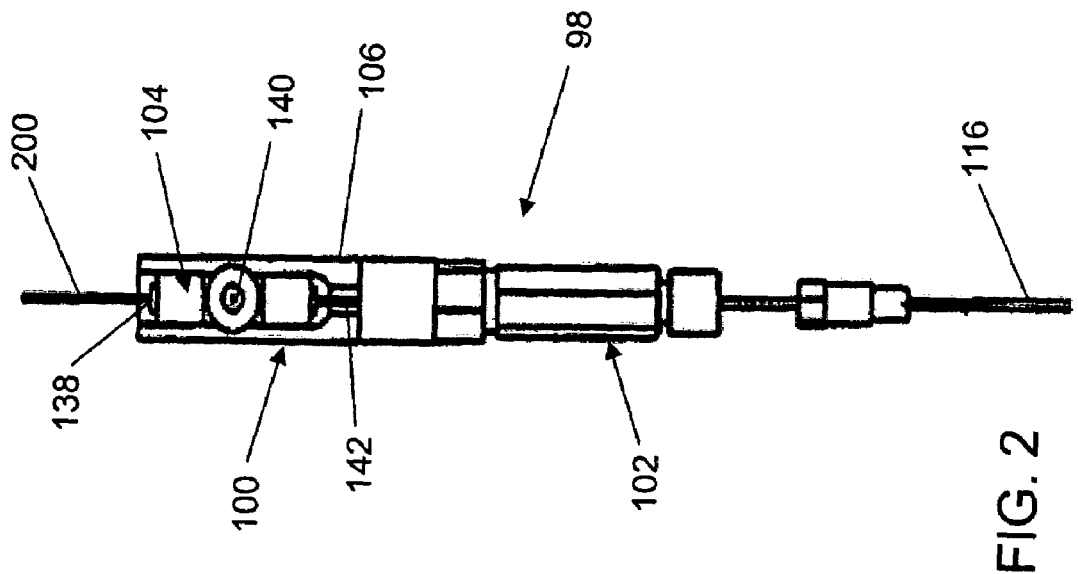
FIG. 1 is a perspective view of an exemplary mixing chamber probe adaptor joined with a mixing chamber and a spring loaded probe.

For the purposes of promoting an understanding of the principles of the invention, reference will be made to the embodiments illustrated in the drawings and specific language will be used to describe the same. Nevertheless, one of skill in the art will understand that reference to the embodiments in the drawings does not limit the scope of the invention. Any alterations and further modifications of the described embodiments, and any further applications of the principles of the invention as described herein are contemplated as would normally occur to one skilled in the art to which the invention relates.

Embodiments of the current invention help ensure proper mixing of analyte with MALDI matrix solution prior to MALDI target spotting. One of skill in the art understands that obtaining proper mixing of analyte and MALDI matrix solution thoroughly and in a correct ratio prior to MALDI target spotting is a major obstacle in obtaining satisfactory results in automated MALDI. Pre-spotting MALDI target preparation, such as mixing analyte and MALDI matrix solution, is crucially important to insure accurate MALDI results. Use of a mixing chamber in connection with a MALDI spotting probe ensures both proper mixing and correct ratios of analyte to matrix solution. When using a mixing chamber, the fluid flow of one or both of the analyte and matrix solution into the mixing chamber controls the amount of mixing and the ratio of analyte to matrix solution. Before the current invention, because of the various problems with tubing disconnections and kinks, this carefully monitored MALDI preparation could not be consistently used with spring-loaded MALDI probes. Embodiments of the mixing chamber probe adaptor, along with preventing kinks and bends in the spring loaded probe tubing, also prevent tubing breaks and tubing disconnections caused as a result of the relative weight placed on the tubing by the use of an unsupported mixing chamber. Due to the present invention, because mixing chambers may be reliably used with a spring loaded probe, the user no longer needs to worry about inexact ratios of analyte and MALDI matrix solution or incomplete mixing.

The carefully controlled mixing resulting from the use of a mixing chamber removes some of the unknown factors generally present in the complexities of MALDI preparation. Advantages achievable when using a mixing chamber allow users of automated MALDI equipment to concentrate on providing the correct type of matrix, concentration of matrix, and/or concentration of analyte. Generally, the choice of a matrix substance used is dependent upon the type of molecule(s) in the analyte. Different matrix substances may be used with different types of biomolecules or different types of polymers. The skilled artisan understands that more than a hundred different matrix substances exist. Many times, MALDI preparation parameters must be individually tested to attain the best possible MALDI target.

The exemplary embodiment of FIG. 1 shows a mixing chamber probe adaptor (100) joined with a spring loaded probe (102) and a mixing chamber (104). One of skill in the art understands that the present invention may be used to join any applicable chamber with a probe. As non-limiting examples, the chambers may be adapted to flush tubing or connect more than a single instrument together; however, certain embodiments of the invention are particularly valuable when used with a mixing chamber. In some embodiments, this mixing chamber will be a micro mixing tee.

In the embodiment shown in FIG. 1, the joining of the mixing chamber and the spring loaded probe is reversible. As one of skill in the art recognizes, the embodiments of the invention that reversibly join the mixing chamber and the spring loaded probe provide benefits such as allowing the individual purchase of replacement parts, allowing different types of mixing chambers and probes to be interconnected, and allowing easy cleaning and sterilization of both the mixing chamber and the probe.

Figure 2:
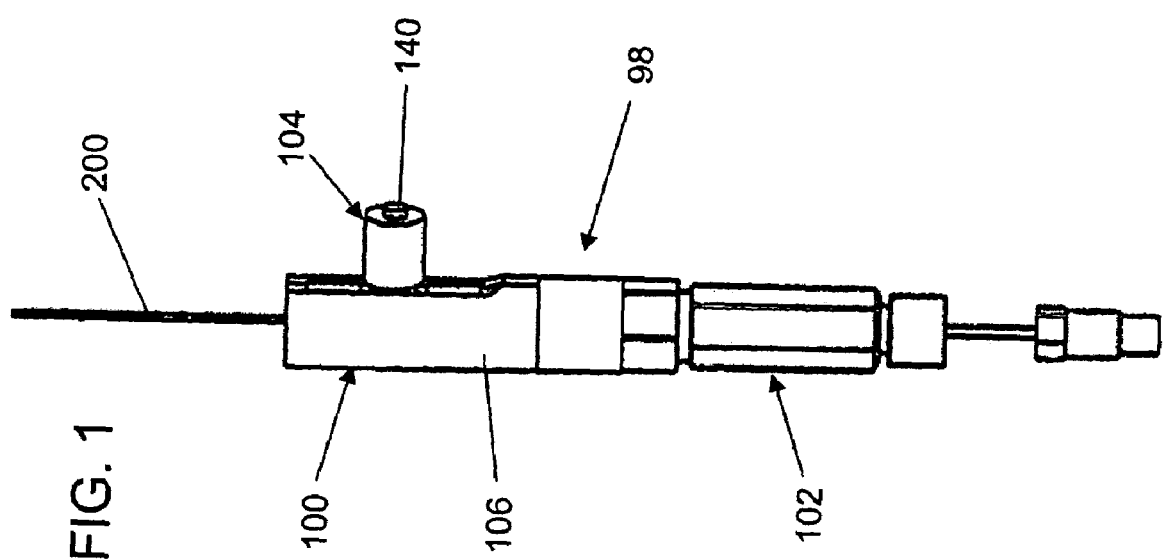
FIG. 2 is a side view of the exemplary embodiment of FIG. 1.

In the embodiment shown in FIGS. 1 and 2, the mixing chamber probe adaptor (100) includes a sleeve (106) that is structured to receive a mixing chamber. The mixing chamber probe adaptor (100) of FIGS. 1 and 2 is especially suited to join mixing chambers and automated MALDI spotting probes. The spring loaded probe (102) may be used to spot MALDI plates as part of an automated MALDI spotting apparatus. The skilled artisan understands that the structure of the spring loaded probe is not exceptionally important, although a particular structural arrangement of a spring loaded probe may affect the shape, size and adaption properties of certain embodiments of the mixing chamber probe adaptor.

FIGS. 1 and 2 show a mixing chamber having a first chamber inlet port (138) tailored to receive tubing that may be capillary tubing (200) carrying analyte, a second chamber inlet port (140) tailored to receive tubing that may be capillary tubing carrying MALDI matrix solution, and a chamber outlet port (142), tailored to receive tubing that may be capillary tubing which transfers analyte sample into the spring-loaded probe (102). Although the embodiment of FIGS. 1 and 2 show two chamber inlet ports and a single chamber outlet port in the mixing chamber, certain embodiments of the invention may be used with mixing chambers having a single chamber inlet port and chamber outlet port, or mixing chambers having a larger number of chamber inlet ports and/or chamber outlet ports. Furthermore, while analyte enters the mixing chamber by the first chamber inlet port in the mixing chamber 104, one of skill in the art understands that analyte and/or matrix may enter the mixing chamber by either the first or the second chamber inlet port.

When used with the present invention, the first chamber inlet port and/or second chamber inlet port of the mixing chamber may have a larger diameter than the chamber outlet port. These distinct diameters allow more consistent flow control of the matrix and analyte mixture and allow the user to reduce the void volume of the tubing in response to the application needs. In certain embodiments of the mixing chamber probe adaptor, changes in the diameter of the chamber inlet ports and chamber outlet port of the mixing chamber will not have an effect on the shape of the mixing chamber probe adaptor. As one of skill in the art understands, the diameter of the chamber inlet ports and chamber outlet port may vary if the mixing chamber probe adaptor is used with a mixing chamber that accepts various different types and sizes of tubing and capillary tubing.

Before mixing with MALDI matrix solution in the mixing chamber, the analyte may be subjected to a liquid chromatography "clean up" in an analyte separation instrument. Generally, an analyte separation instrument may encompass any instrument used to separate analyte into specific fractions. The analyte separation instrument may separate analyte into fractions based on size, charge, or the like. One example of an analyte separation instrument may be a chromatographer, such as a liquid chromatographer. Another example of an analyte separation instrument may be a two-dimensional gel apparatus. When an analyte separation instrument is used with certain embodiments of the invention, the mixing chamber probe adaptor, by receiving and supporting the mixing chamber, permits the mixing chamber to supply support for tubing coming from the analyte separation instrument, such as a liquid chromatography apparatus, into a chamber inlet port. This support allows the coupling of an automated liquid chromatography apparatus to an automated MALDI target spotting apparatus. Generally, following the liquid chromatography "clean-up," which is commonly automated high performance liquid chromatography (HPLC), tubing transfers the "cleaned-up" analyte directly from the liquid chromatographer to the mixing chamber.

Embodiments of the invention support a mixing chamber receiving analyte flowing directly from an analyte separation instrument, such as a HPLC apparatus. These embodiments ensure that the tubing coming from an instrument output port of the analyte separation instrument does not disconnect or kink when it enters the mixing chamber. Certain advantages exist because the current invention permits automated HPLC to be coupled in-line to automatic MALDI spotting. The advantages of using analyte directly from an HPLC include, but are not limited to, saving time, saving analyte sample, and recovering purer analyte. There is also the benefit of preserving the HPLC run, as in-line coupling of HPLC and MALDI essentially captures the HPLC run on a plate for further analysis. Regardless of these advantages, the skilled artisan understands that when used with certain embodiments of the invention, the analyte need not be subjected to "clean-up" procedures. In certain other embodiments, the analyte may be subjected to alternative "clean up" methods such as 2-dimensional gel electrophoresis and solid phase extraction. Any of these methods may be in-line coupled to automated MALDI target spotting. The skilled artisan understands that the previous examples of "clean-up" methods serve an illustrative purpose and are meant to be non-limiting as any type of analyte "clean-up" method known in the art may be used with the current invention and in certain embodiments, more than one "clean-up" procedure is envisioned.

Figure 3:
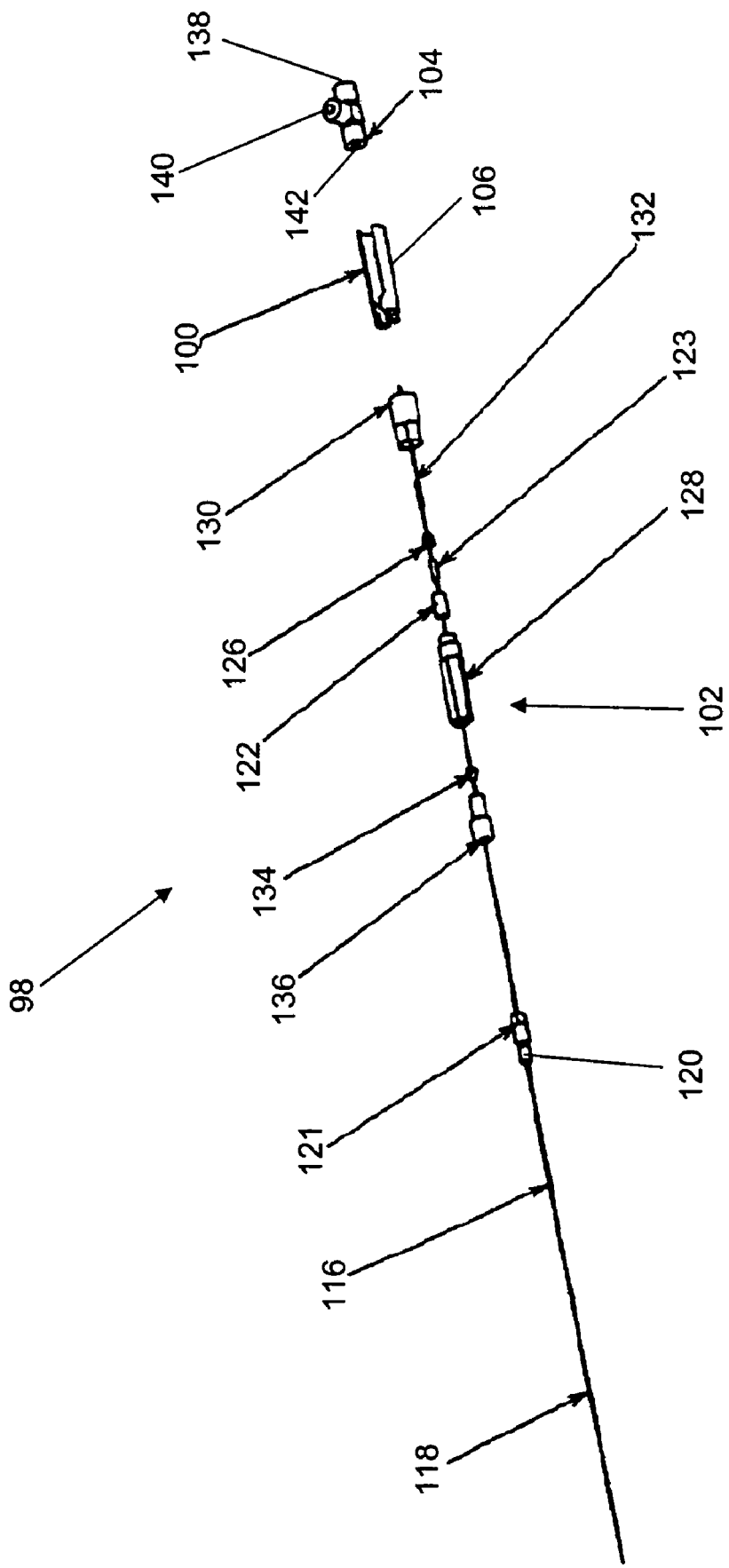
FIG. 3 is a disassembled view of the exemplary embodiment of FIG. 1.
Figure 4:
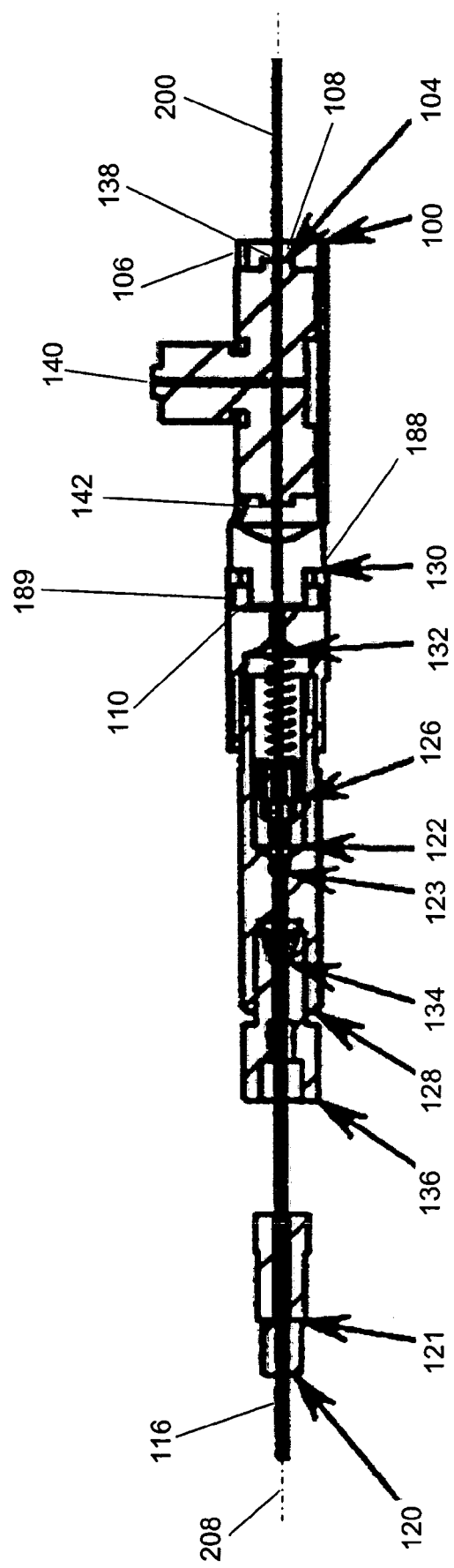
FIG. 4 is a cross sectional view of the exemplary embodiment of FIG. 1.

FIG. 3 shows a disassembled view of the mixing chamber probe adaptor (100), the spring loaded probe (102), and the mixing chamber (104). The spring loaded probe comprises a spring probe sleeve (116) that fits over tubing (118), a fitting tube (120), a threaded probe nut (121), a nut (136), a ferrule (134), a spring probe cartridge (128), a limit restrictor coupling (122), a tube compression sleeve (123), a flush nut (126), a spring (132), and a spring probe cartridge cap (130). The tubing (118) may be capillary tubing that comes from the mixing chamber (104). As shown with reference to the assembled cross-sectional view of FIG. 4, the fitting tube (120) acts as a stop for the threaded probe nut (121) and secures the probe inside the probe guide. The nut (136) connects the spring probe sleeve (116) with the spring probe cartridge (128). The ferrule (134) prevents tubing kinks within the spring probe cartridge (128). The limit restrictor coupling (122) houses the tube compression sleeve (123) and the flush nut (126). The mixing chamber probe adaptor (100) includes a probe connector (110). The spring probe cartridge cap (130) includes a hollow top female portion (189) that is adapted to accept the connector (110) of the mixing chamber probe adaptor (100). The hollow top female portion (189) of the spring probe cartridge cap (130) includes a shoulder (188) that holds the connector (110) in the hollow top female portion (189).

Figure 8:
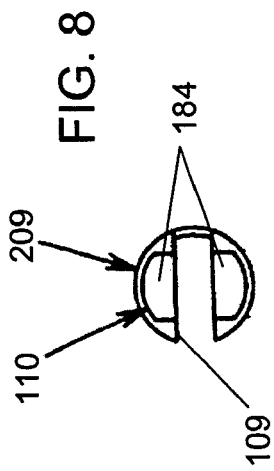
FIG. 8 is a bottom view of the exemplary mixing chamber probe adaptor of FIG. 1.
Figure 5:
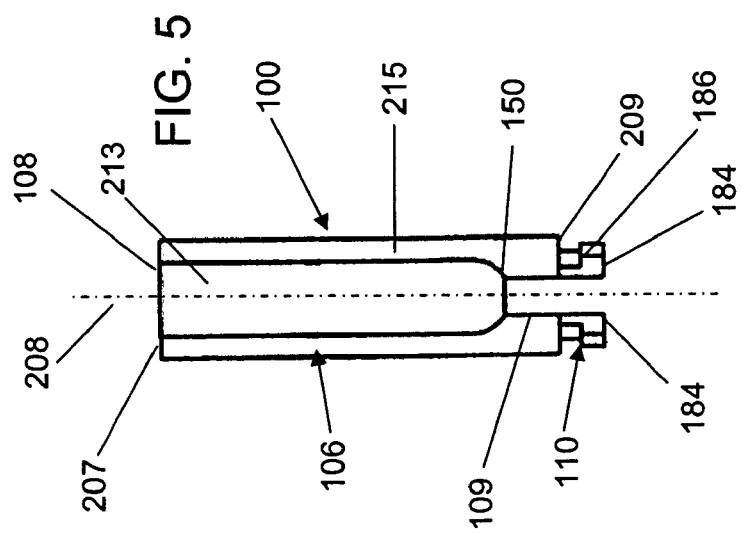
FIG. 5 is a side view of the exemplary mixing chamber probe adaptor of FIG. 1.

As shown with reference to the assembled cross-sectional view of FIG. 5, the mixing chamber probe adaptor (100) includes, but is not limited to, the sleeve (106) and the probe connector (110). The sleeve (106) comprises a chamber connector (108). In an exemplary embodiment, the sleeve (106) has a C-shaped edge as best seen in the top view of FIG. 7 and the bottom view of FIG. 8. The sleeve (106) has a C-shaped outer wall (213), a first end (207), a second end (209), side walls (215), and a cup-shaped edge (150). The connector (110) is integrally formed with the sleeve (106) and protrudes from the second end (209) of the sleeve (106). The cup-shaped edge (150) includes a slot (109) that accepts the chamber outlet port (142) and allows passage of the tubing 118. The mixing chamber probe adaptor (100) also includes a cavity formed by the C-shaped outer wall (213), the side walls (215), and the cup-shaped edge (150) as best seen in the cross sectional view of FIG. 6. The cavity is generally shaped to allow a mixing chamber to be placed in the cavity. In this manner, the mixing chamber probe adaptor (100) helps maintain the mixing chamber (104) in a fixed position with respect to the probe (102). The advantage of keeping the mixing chamber (104) in a fixed position goes to the underlying importance of having a mixing chamber probe adaptor (100) that prevents strain and kinks in the tubing coming into the probe. The spatial relationship between the mixing chamber (104) and the probe (102) should be maintained to prevent strain on or kinks in the tubing. Thus, the chamber probe adaptor, and more specifically the mixing chamber probe adaptor, holds the chamber and the probe in a fixed spatial relationship. Frequently, this fixed spatial relationship will refer to the position of an outlet port of the chamber and an inlet port of the probe.

The connector (110) includes two projections (184) for mating with the hollow top female portion (189). The skilled artisan understands that other embodiments of the mixing chamber probe adaptor may include inwardly projecting shoulders or other joining means on the connector (110). The projections (184) may be pressed together until they fit into the hollow top female portion (189) of the spring probe cartridge cap (130). Once the projections (184) have been placed in the hollow top female portion (189) of the spring probe cartridge cap (130), the projections (184) may be released from the inward pressure. Releasing the inward pressure permits outward movement of the projections (184) thus allowing the outwardly projecting shoulders of the projections (184) to come into abutment with the shoulder (188) in the hollow top female portion (189) of the spring probe cartridge cap (130). This abutment keeps the mixing chamber probe adaptor (100) securely fastened to the spring loaded probe (102).

Figure 6:
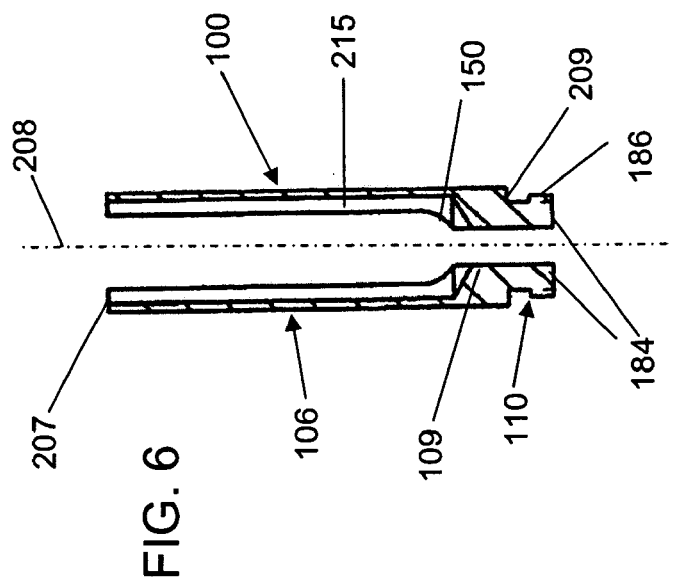
FIG. 6 is a side cross-sectional view of the exemplary mixing chamber probe adaptor of FIG. 1.
Figure 7:
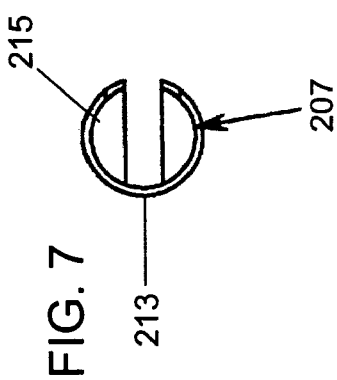
FIG. 7 is a top view of the exemplary mixing chamber probe adaptor of FIG. 1.

In the embodiment shown in FIG. 6, the probe connector (110) has a male portion that includes the two projections (184) separated by a back slot. In certain embodiments, the number of projections may be less than or greater than two. For example, a single projection that fits into a probe using friction may be used. Each projection (184) is generally semi-circularly shaped with outward projecting shoulders (186). The back slot in the connector (110) may extend, for example, approximately one-seventh of the way up the longitudinal axis (208) of the mixing chamber probe adaptor (100) from the projections (184). In certain embodiments, this back slot (213) permits pressure to be placed on the projections (184) so that the outward projecting shoulders (186) of the projections (184) can be brought toward each other in a movement (188) substantially perpendicular to the longitudinal axis (208) of the mixing chamber probe adaptor. This movement allows easy attachment and de-attachment of the mixing chamber probe adaptor with the spring loaded probe cartridge. Easy reversible connection of the mixing chamber and probe allows interconnection of parts having different desired traits, easy cleaning, and individual part replacement.

As one of skill in the art understands, the projections of the mixing chamber probe adaptor may be constructed in any shape that allows secure fastening to a probe. Thus, if the cartridge of the probe is a square shape, the projections can be easily adapted from semi-circles to semi-squares. Furthermore, depending upon the shape of the shoulder in the spring-loaded probe cartridge, the depth of the shoulder of the projections on the mixing chamber probe adaptor may be altered. Additionally, the mixing chamber probe adaptor may freely rotate in a circular motion inside the spring probe cartridge cap. In some embodiments, this rotational movement is not possible. In some embodiments, the connector will be easy to attach and de-attach (such as those shown) to the probe using only manual strength. In alternative embodiments, the connector may comprise, for example, a screw or hook type assembly.

Although the mixing chamber probe adaptor (100) in the exemplary embodiment is a C-shaped sleeve, one of skill in the art understands that many different types and shapes of chamber connectors may be used in certain embodiments of the present invention. These various embodiments may depend upon the shapes and sizes of the mixing chambers and the probes with which they are designed to be used. The skilled artisan will understand when to chose a particular type and/or shape of chamber connector. Although the cavity formed by the sleeve (106) runs along the longitudinal axis (208) of the mixing chamber probe adaptor, the opening for receiving the mixing chamber is not so limited and any opening that allows joining of a mixing chamber and a probe is contemplated. A non-limiting example may include a cavity running along a horizontal axis of the mixing chamber probe adaptor.

By joining the mixing chamber to a sample dispensing probe, such as a MALDI spotting probe, embodiments of the present invention provide the previous advantages through a simple design. One of skill in the art will understand that any applicable housing may be used in lieu of a sleeve. For example, the housing may be rectangularly shaped. Furthermore, the cavity may be any shape generally adapted to receive a mixing chamber. Moreover, the skilled artisan understands that the outside of the housing and the cavity need not be of corresponding shape. For example, the housing may have an exterior surface with a rectangular cross-section but a cavity with a circular or semi-circular cross-section.

One of skill in the art understands that a mixing chamber made from various materials may function with embodiments of the invention. In certain embodiments, the mixing chamber probe adaptor will be made from a single piece of molded material. In this case, the chamber probe adaptor will have a first chamber probe adaptor end comprising the chamber connector and a second chamber probe adaptor end comprising the probe connector. In alternative embodiments, pieces of the mixing chamber probe adaptor, such as the C-shaped sleeve and connector may be made of different materials. When used with some embodiments, the mixing chamber will be made from biocompatible, chemically resistant material such as polyetheretherketone (PEEK). Certain changes in the mixing chamber may result in different designs for the mixing chamber probe adaptor. For example, depending on the type of material used to manufacture the mixing chamber, the mixing chamber probe adaptor may need to be suitably adapted. Thus, as a non-limiting example, if the mixing chamber is made from a material that generates heat, the mixing chamber probe adaptor may need to be made of a heat resistant material. Nevertheless, one of skill in the art understands that the mixing chamber probe adaptor may be made from a variety of materials. These materials may include, but are not limited to plastics, such as PEEK, Teflon and Teflon derivatives, and metals. In some embodiments, in order to allow flexibility in attaching the mixing chamber probe adaptor to the probe, the mixing chamber probe adaptor is made of flexible plastic, such as PEEK. In other embodiments, the mixing chamber probe adaptor may be made from flexible metals.

Changing the size of the mixing chamber, such as minimizing the mixing chamber to decrease the total amount of dead volume in the system may require the mixing chamber probe adaptor to be suitably adapted. In some embodiments, a smaller mixing chamber and mixing chamber probe adaptor may be advantageous because of the resultant decrease in dead volume. Generally, decreasing the dead volume is a major goal of automated MALDI spotting. A lower dead volume prevents MALDI peak spreading and ensures concentrated analyte sample spotting. One of skill in the art will understand when it may be beneficial to adapt either the material or the size of the mixing chamber probe adaptor.

It is also possible to adapt embodiments of the mixing chamber probe adaptor (100) to other changes in the mixing chamber (104). As such, the skilled artisan recognizes that the mixing chamber probe adaptor (100) may be adapted to different shaped mixing chambers. T-shaped mixing chambers, such as the mixing chamber shown in FIGS. 1-4, are well known in the art and can be purchased commercially from companies such as Upchurch Scientific, Oak Harbor, Wash. Although the mixing chamber shown in the figures is T-shaped, one of skill in the art will recognize that the invention contemplates any mixing chamber that can be joined to a probe using the chamber probe adapter. For example, certain embodiments may be adapted to accept an E-shaped chamber or a chamber having 45 degree chamber inlet port introduction angles.

Those knowledgeable in the art will appreciate that the device of the invention may also lead to numerous additional benefits and advantages. Moreover, those knowledgeable in the art will appreciate that the exemplary devices of the invention shown and described herein are but exemplary embodiments, and that many equivalent and alternative embodiments exist within the scope of the invention. Accordingly, discussion made herein should not be interpreted as a limitation of the scope of the claimed invention.

While exemplary embodiments have been illustrated and described, it should be understood that changes and modifications can be made therein in accordance with ordinary skill in the art without departing from the invention in its broader aspects as defined in the following claims.

What is claimed is:

1. A coupled analyte separation and spectrometry device comprising:
   (a) an analyte separation instrument comprising an instrument outlet port through which separated analyte samples exit the instrument;
   (b) a sample dispensing probe for dispensing analyte samples onto a substrate, the sample dispensing probe comprising a probe inlet port for accepting analyte samples;
   (c) a chamber disposed between the analyte separation instrument and the sample dispensing probe, the chamber comprising a first chamber inlet port in fluid communication with the instrument outlet port, a second chamber inlet port, and a chamber outlet port connected to the probe inlet port, wherein the second chamber inlet port is in fluid communication with a source of matrix solution, and further wherein the chamber serves as a mixing chamber for the analyte sample from the analyte separation instrument and the matrix solution; and
   (d) a chamber probe adaptor comprising a chamber connector adapted to connect to the chamber and a probe connector adapted to connect to the sample dispensing probe;
   wherein the chamber probe adaptor comprises a sleeve that defines an internal cavity adapted to hold the chamber, and further wherein the chamber probe adaptor holds the chamber outlet port and the probe inlet port in a fixed spatial relationship.

2. The device of claim 1, wherein the chamber outlet port is connected to the probe inlet port by tubing.

3. The device of claim 1, wherein the matrix solution is a MALDI matrix solution.

4. The device of claim 1, wherein the analyte separation instrument is a liquid chromatography apparatus, and the sample dispensing probe is a MALDI target spotting probe.

5. The device of claim 4, wherein the MALDI target spotting probe is a spring loaded probe.

6. The device of claim 1, wherein the chamber is a T-shaped chamber.

7. The device of claim 1, wherein the probe connector is integrally formed with the chamber connector.

8. The device of claim 1, wherein the internal cavity has a tubular cross-section.

9. The adaptor of claim 8, wherein the sleeve comprises a C-shaped outer wall.

10. The adaptor of claim 7, wherein the probe connector comprises a male portion having at least one projection adapted to connect to the sample dispensing probe.

11. The adaptor of claim 10, wherein the male portion comprises two projections.

12. The adaptor of claim 11, wherein the two projections are separated by a gap.

13. The adaptor of claim 12, wherein the gap allows the two projections to move toward each other.

14. The adaptor of claim 10, wherein the at least one projection comprises outward projecting shoulders.

15. The device of claim 1, wherein the chamber connector and the probe connector are made from PEEK.

16. A method of automatic spotting of MALDI plates comprising spotting a MALDI target with a sample dispensing probe connected to the chamber probe adaptor of claim 1.

17. The method of claim 16, wherein the sample dispensing probe is a spring loaded probe.

* * * * *